(12) United States Patent
Farris et al.

(10) Patent No.: US 7,792,687 B2
(45) Date of Patent: *Sep. 7, 2010

(54) MEDICAL CLAIMS EVALUATION AND CORRECTION SYSTEM

(76) Inventors: Alex Farris, 1960 Highway 33, Pelham, AL (US) 35124; Martin C. Nowak, 309 Tutwiler Dr., Trussville, AL (US) 35173

( * ) Notice: Subject to any disclaimer, the term of this patent is extended or adjusted under 35 U.S.C. 154(b) by 538 days.

This patent is subject to a terminal disclaimer.

(21) Appl. No.: 11/679,547

(22) Filed: Feb. 27, 2007

(65) Prior Publication Data

US 2007/0265883 A1    Nov. 15, 2007

Related U.S. Application Data

(63) Continuation-in-part of application No. 11/160,399, filed on Jun. 22, 2005.

(51) Int. Cl.
*G06Q 10/00* (2006.01)
*G06Q 50/00* (2006.01)

(52) U.S. Cl. ........................................................ 705/2

(58) Field of Classification Search ................ 705/2, 705/3

See application file for complete search history.

(56) References Cited

U.S. PATENT DOCUMENTS

| | | | | |
|---|---|---|---|---|
| 4,667,292 | A * | 5/1987 | Mohlenbrock et al. | 705/2 |
| 6,826,536 | B1 * | 11/2004 | Forman | 705/4 |
| 2002/0138304 | A1 * | 9/2002 | Fontanesi | 705/2 |
| 2004/0024749 | A1 * | 2/2004 | Kusens | 707/3 |
| 2004/0078228 | A1 * | 4/2004 | Fitzgerald et al. | 705/2 |
| 2004/0172282 | A1 * | 9/2004 | Benja-Athon | 705/2 |

* cited by examiner

*Primary Examiner*—Gerald J. O'Connor
*Assistant Examiner*—Trang Nguyen
(74) *Attorney, Agent, or Firm*—Smith, Gambrell & Russell

(57) ABSTRACT

A method for controlling healthcare costs comprising creating associational databases in a computer system containing physician, hospital, patient and payer information; cross-referencing and searching said databases for specific occurrences of treatment, discharge, or transfers with characteristics leading to higher medical costs, and providing statistical information to payers on specific physicians and hospitals such that payer's can determine whether to retain such providers services for specific procedures.

7 Claims, 4 Drawing Sheets

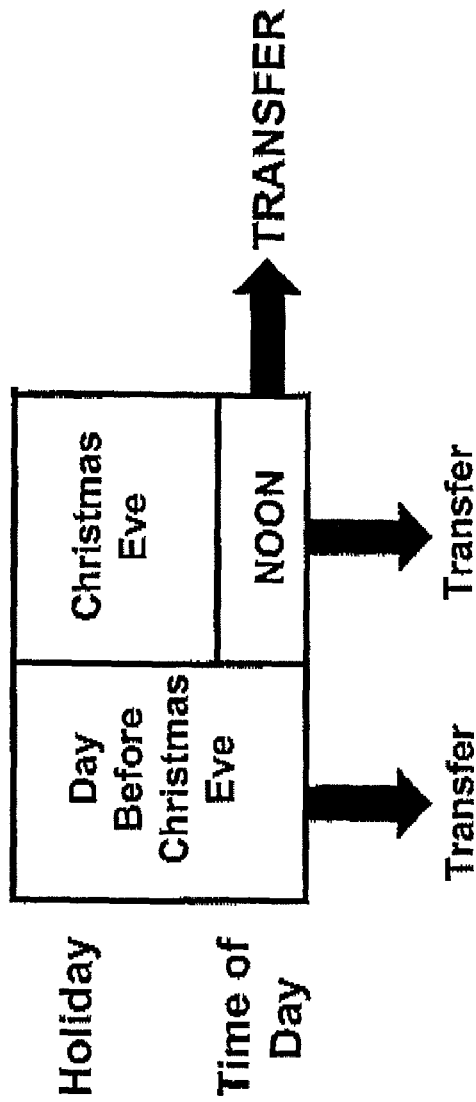

MEDICAL CLAIMS EVALUATION AND CORRECTION SYSTEM

CROSS REFERENCE TO RELATED APPLICATION

This application is a continuation-in-part of application Ser. No. 11/160,399, filed Jun. 22, 2005 and which is being incorporated in its entirety herein by reference.

FIELD OF THE INVENTION

The present invention relates generally to the field of healthcare and more particularly to the areas of practice quality and cost containment. In greater particularity the present invention relates to the reduction in multiple iterations of the same procedures by practitioners with a historic proclivity towards repeat surgeries or other procedures. In even greater particularity the present invention relates to a method for identifying repeat surgeries and their sources and causes. In even greater particularity the present invention relates to the identification of multiple, serial insurance claims, and grouping of claims, to determine patterns of multiple iterations of procedures or surgeries on the same patient, or groups of patients to identify a common practitioner source or common provider facility source. In like manner the present invention relates to the identification of multiple serial insurance claims, and grouping of claims, to determine patterns of health complications following admission, procedures, treatments, interventions, surgeries and the like on the same patient or groups of patients, to identify a common practitioner source or provider facility source of such complications. In even greater particularity the present invention relates to a method for identifying repeat procedures and surgeries or complication and their sources and causes. In another aspect of the invention, the invention relates to patterns of patient transfers from one provider to another based on insurance specific or date specific rules. In greater particularity the present invention enables the identification of provider transfers by date and time relative to eh expiration of insurance coverage or the convenience of the provider.

Increasing medical costs and insurance costs are one of the leading sources of concern for people of all ages and businesses of all sizes as well as Federal, State and local governments. This includes physicians groups, hospitals, healthcare providers of all types including nursing homes and outpatient facilities, insurers, government agencies, labor groups and investment groups. For the past several decades the rising cost of healthcare and insurance have eaten away at the value of the earnings of all groups. Historically, the trend has been to advise that more research, better facilities, technological advances, and more doctors would solve the dilemma or that public education on medical practices would improve the quality of care patients would expect. All of these things contribute to improving the system, but the rising cost remains unchecked.

SUMMARY OF THE PRESENT INVENTION

This invention addresses sources of medical and insurance costs that can be eliminated or greatly reduced. The savings realized by the implementation of the invention could significantly reduce or even abate the rise in medical and insurance costs. In principal the present invention is based on the understanding that not all patients receive the same quality of care and that not all practitioners have the same level of skill or dedication, even though the practitioner and patient have no statistical tools to evaluate the quality of care or the level of skill. Consequently, among patients for whom a lower quality of care is provided greater instances of repeat surgeries are performed, or repeat hospitalizations for the same condition, or repeat treatments or surgeries for the same underlying condition which lead to increased complications impacting the quality of the patients life, increased billing by the physician or subsequent physicians at the same or subsequent facilities and increased cost to the insurers and insured patients.

Further, the present invention is also based on the realization that financial motives prompt patient discharges which result in increased overall costs due to repetitive procedures at the transferee provider facilities.

The present invention contemplates the use of a dynamic database that will provide the statistical and analytical data for use in identifying the sources of sub-quality care or skill whether by a practitioner or a provider facility. The identification of these sources coupled with the subsequent refusal of services to such sources will cause the sources to improve their services or turn to other endeavors, both of which results in improved healthcare and decreased costs.

Accordingly, the present invention contemplates patient specific data from hospital or insurance records that will identify the nature of the patient's illness, the treating physician and facility, the course of treatment, for the illness, and any recurrences of the illnesses. By way of example, patients suffering from a degenerative joint disease may eventually require joint replacement surgery. If a sufficiently large group of patients having such disease can be monitored and historical data maintained with reference to the treating physician and facility, then trends can be documented and physicians or facilities that treat the patients in will have an independent cross referenced record of outcome. More specifically, physicians or facilities that perform abnormally high repeat surgeries or refer excessive numbers of patients to other surgeons for follow up treatment on the previously "repaired" joint can be identified. In a further modification of the invention, statistical analysis can be performed relative to temporal variations in care by observing and quantifying factors such as the time of day or day of week of events such as transfers from ward to ward or facility to facility.

In a still further variation of the invention biographical and institutional data on facilities can be quantified to determine whether background factors in competency and care can be identified. Each of these quantifications makes it possible for the health care user or insurer to screen physicians and facilities to determine whether the patient should submit to treatment or seek treatment elsewhere. The concept is not to obtain a second opinion regarding the patient, but rather an accurate measure on the level of care to be expected by the patient and the parameters that define the duration of care and termination of care.

These and other objects and advantages of the invention will become apparent from the following detailed description of the preferred embodiment of the invention.

BRIEF DESCRIPTION OF THE DRAWINGS

An flow chart for the method of the present invention is depicted in the accompanying drawings which form a portion of this disclosure and wherein:

FIG. 4 is a holiday correlation chart for transfers.

DESCRIPTION OF THE PREFERRED EMBODIMENT

Figure 1:
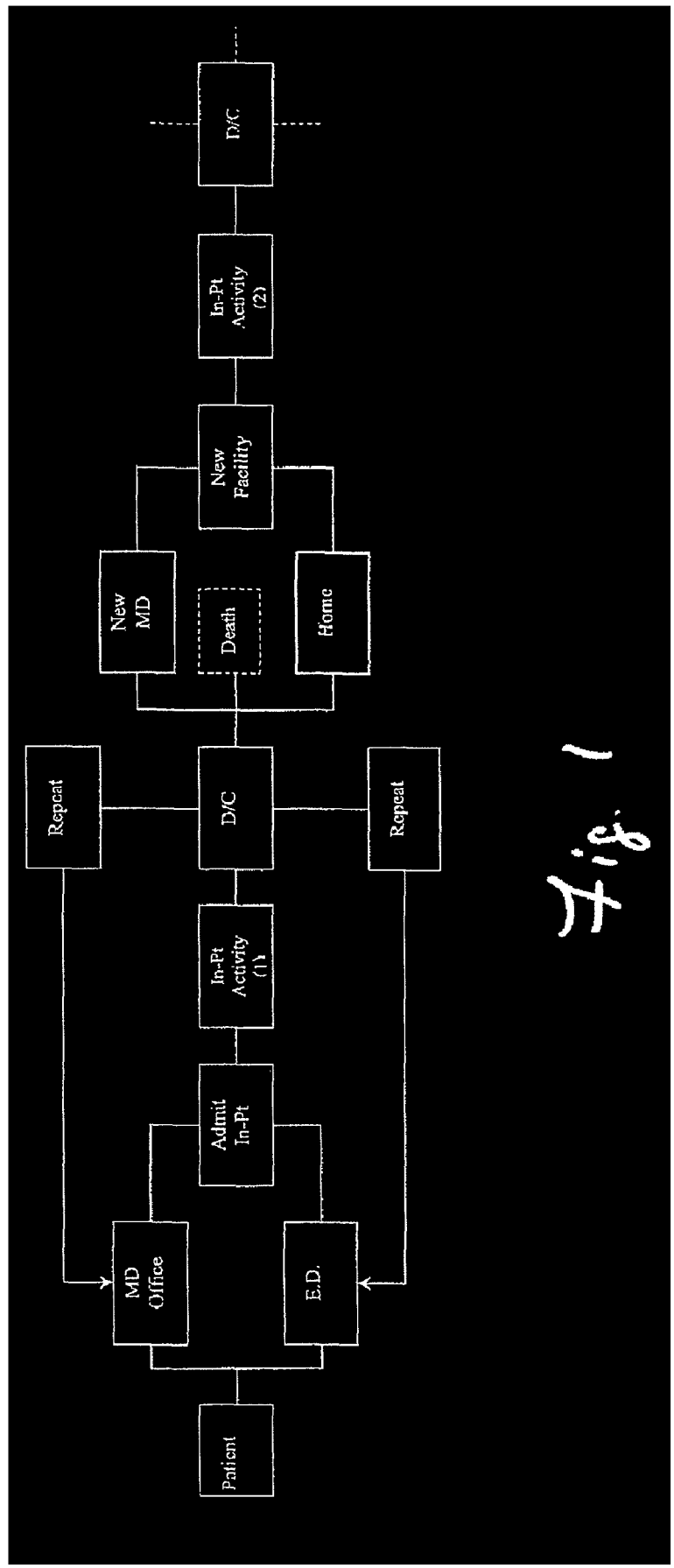
FIG. 1 is an in patient flow diagram of events which may be tracked by the system.
Figure 2:
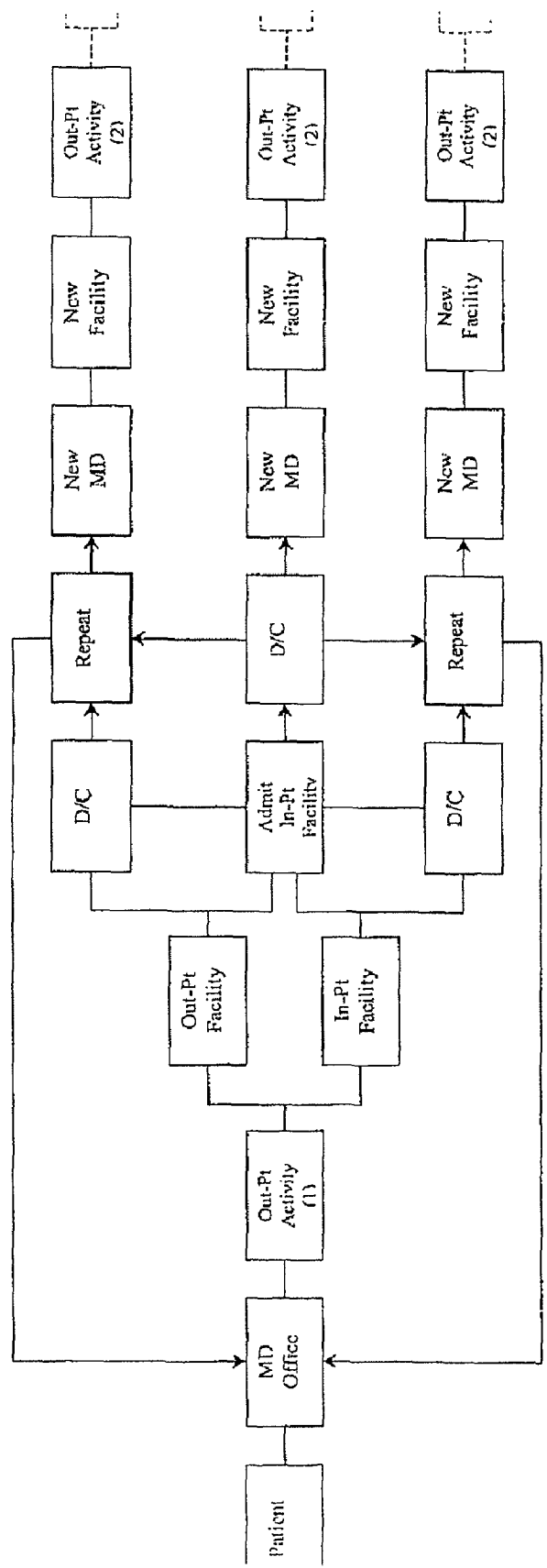
FIG. 2 is an out patient flow diagram of events which may be tracked by the system.

As illustrated in the accompanying figures, the present invention utilizes a database P maintained in a memory of a computer in which discrete pieces of data are collected. The term computer includes mainframe computers, personal computers, or a network of computers. The term a memory means a physical component of a computer or network of computers designed to store information and allow its retrieval and use of the stored information. Retrieval and use is accomplished by a software program that searches and correlates data as defined by the user of the system. The parameters discussed herein are used in such search an correlation software, however, the specific software program may vary depending on the platform it is running on, the type of network it is deployed in, the number of electronic addresses each memory component utilizes and a myriad of factors that are within the knowledge of a software designer who would be expected to create such software taking into consideration the specific configuration of the associated hardware.

Each patient presenting to a practitioner for treatment currently provides by necessity information regarding the persons identity, age, race, and medical conditions. This information is usually transmitted by the practitioner to an insurer or a government guarantor for payment. In so doing, the practitioner also provides identifying information about itself as well as the diagnosis and treatment provided to the patient on a specific date. All of this data is available in electronic or near electronic form as it is processed by the insurers or guarantors. Each patient can be universally identified by a code such as the patient's social security number. Each healthcare provider can be likewise identified by SSN or taxpayer id or some other unique reference.

Database P includes a permanent file identified with each patient including patient identification and the nature of each occurrence of illness or injury for which the patient has been treated. The information can be transmitted to the database via an interconnected computer network such as the Internet, Local area network, Wide area network, wireless network, so that data on the same patient may be sent from anywhere the network reaches to the memory containing database P. For each injury or illness transmitted to the database, data on the date, treatment and identity of the healthcare provider or facility will also be included. Accordingly, the minimum data fields required for the system include:

Patient id such as social security number

Facility ID such as Employer tax id number

Procedure ID such as AMA procedure identifier

Date and time of each consultation, admission, referral, transfer, discharge, or procedure.

Cost of each procedure

Paying party Id such as insurance contract number

Patient data files would include fields for each of the above such that each time patient 121-21-2121 is seen by a physician AL12345 at hospital EI 55-55555 and treated for procedure 033333, a record of the date Jan. 1, 2003 and the cost $500 is created showing that payer BC98765-4 paid for the procedure. Each time procedure 033333 is performed on patient 121-21-2121 another record is created in the patient data file with all of the above information. Accordingly a search query of the database can reveal matches for all patients having repeats of the same procedure. Further refinement of the search allows for determination of patients having repeat procedures wherein the procedure was originally performed by the same physician or at the same facility. Each physician in the database can then be searched to determine such things as percentage of repeat procedures on patients or percentage of referrals to other physicians for repeat procedure or remediation of procedures that proved ineffective.

Using the database in this way, a non-biased profile can be created for any physician, facility, or patient. For each physician who performs like procedures, for example arthroscopy, a peer group analysis can be performed, such that each physician can be evaluated as to his standing within the peer group in terms of percentage of repeat procedures or referrals for repeat procedures. By including biographical data on physicians such as medical school, residencies, training rotations, the analysis also provides for analysis of facility effectiveness in training.

The data gathering and sampling aspect of the invention is the precursor to the effective utilization of the invention to reduce costs. Each payer enrolled in the program requires each physician or facility that receives reimbursement from the payer to enroll in the system. Each payer then receives periodic reports identifying each physician or facility whose performance as measured by repeat procedures or referrals for repeat procedures is significantly out of the acceptable range as measured against all other physicians who are expected to have the same skill set. That is to say, internists are measured with internist, podiatrist with podiatrists, cardiovascular surgeons with cardiovascular surgeons, psychiatrist with psychiatrist and so on. The payer then has data with which to evaluate the physicians and make recommendations, such as that physician AL12345 should refrain from performing initial procedures of a certain type or that such procedures should not be performed at facility EI98765-4. Physician AL12345 may thus continue to diagnose and attend to the care of his patients, however, procedures which his performance leads to an inordinate number or repeats would no longer be reimbursable to him by the payer who would advise the facilities utilized by the patients of this fact. For outpatient procedures, the invention requires pre-approval of all procedures by the payer, thus physicians with diagnostic only payment authorization could not receive approval from their payer Additional factors may also be introduced and tracked with the system including such variables as Length of Stay prior to first discharge for a recurrent treatment, Length of Stay prior to first tracked event; Length of Stay after first tracked event; Length of Stay in subsequent facility; Length of Stay prior to next traced event; Length of Stay after next tracked event. Likewise additional measures can be determined such as mortality rates by physician, facility, activity, or iteration of treatment; physician demographics such as medical school, residency, mentors, year group, experience; or facility demographics such as awards, staffing, licensure, income; and other variables as deemed appropriate.

Figures 3A, 3B:
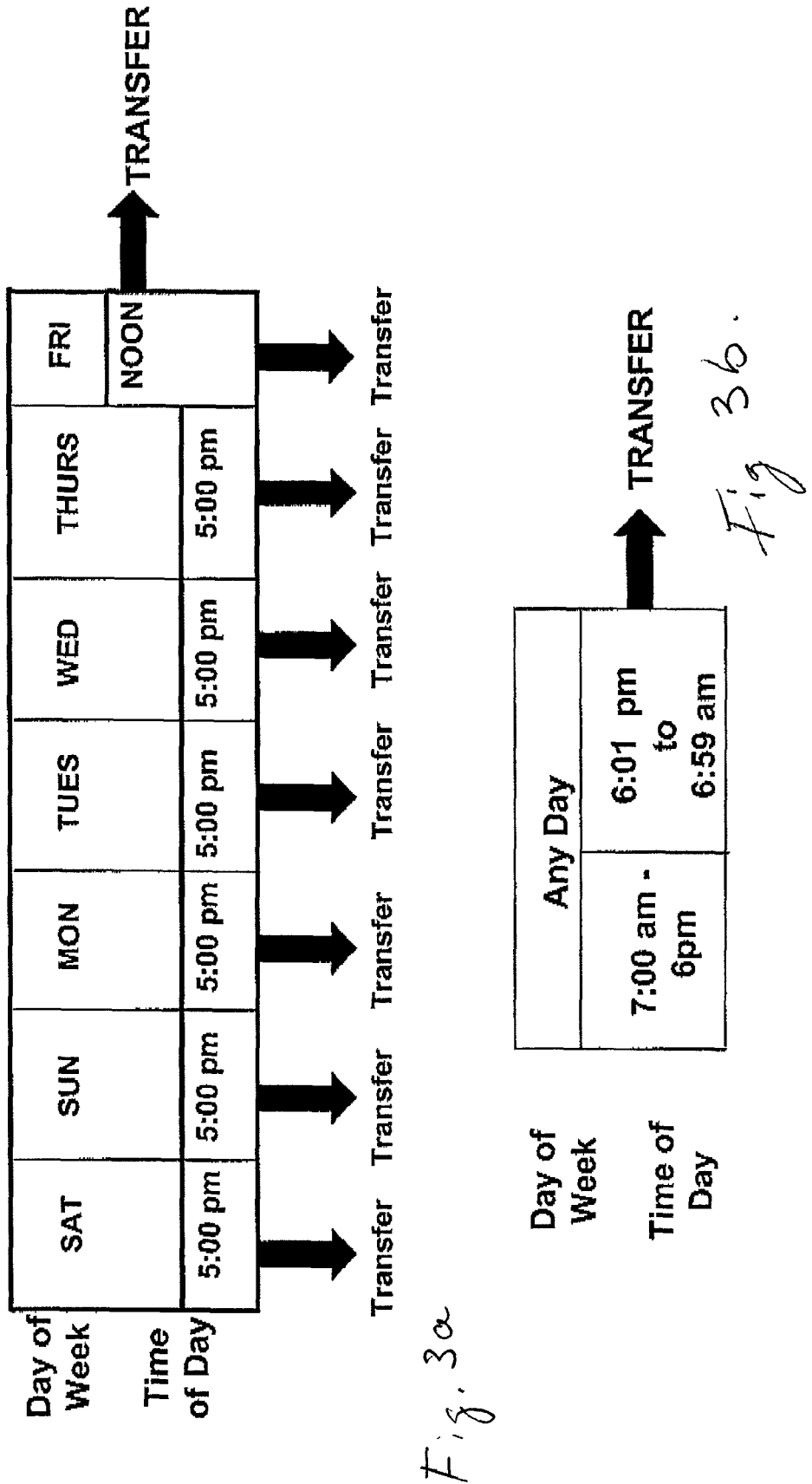
FIG. 3a is a time of day/day of week
FIG. 3b is a time of day correlation chart for transfers.

With respect to FIG. 3, this represents an expected situation which could be revealed or confirmed through the use of the present invention. Specifically, using the database to correlate discharge times of patients from facilities based on non-treatment related events, such as the expiration of insurance, the time of day, the approach of a holiday, the scheduled recreational events of the provider. In FIG. 3, the hypothesis is that more patients will be transferred after 5 PM and before 7 AM on most days and shortly afternoon on weekends. Such transfer procedures in and of themselves place a burden on the transferee facility and concomitantly diminish the equality of patient care. Identification of provider transfer patterns can a allow a payer to proscribe and penalize improvident transfers. By way of example, in certain instances reimbursed care for certain individuals is limited to a matter of days, after which there provider hospital and/or physician receives no further compensation or compensation at a diminished rate. The present invention provides a searchable database which will identify any provider who routinely treats such patients for the maximum compensated period and then transfers patients to a second provider on or near the last day of compensation In many cases the transferee provider must run repetitive lab tests or x-rays to determine the proper treatment modality because the transfer did not include the documentation from the transferor hospital or the transferee provider protocol requires admission testing irrespective of the existence of documentation. These transfers are believed to occur primarily at the times shown in FIGS. 3 and 4.

In practice the system would employ a variation of the following method. Creating a searchable electronic database containing patient, provider, and payer information as described above including the maximum compensable time and rate for each payer; electronically updating the searchable database for each admission, discharge, or transfer of a patient; determining the length of stay for each patient in each facility prior to transfer to another facility; iteratively executing a database management software program correlating the length of stay for each patient with the patients payer and payer's maximum compensable time and/or rate; iteratively executing a software routine for determining a profile for each provider showing transfer histories of patients based on time of day, day of week, proximity to holiday, and payer compensable time and or/rate; periodically providing such provider profiles to payer for review. They system may also be queried on the basis of transferee provider to identify repetitive procedures as noted above to quantify duplicative costs associated with the transfers.

It is to be understood that the form of the invention shown is a preferred embodiment thereof and that various changes and modifications may be made therein without departing from the spirit of the invention or scope as defined in the following claims.

What is claimed is:

1. A method for measuring iterative medical procedures by provider comprising the steps of:
   a. creating a procedures database of identified medical procedures in an accessible system memory on a programmable general purpose computer;
   b. creating a provider database by associating individual medical providers with a unique identifier in said provider database in an accessible system memory on said programmable general purpose computer;
   c. creating a patient database by associating individual patients with a unique identifier in said patient database in an accessible system memory on said programmable general purpose computer;
   d. deriving anecdotal data for storage in said patient database from sequential medical payment claims made to a payer relating to an individual patient within a given time frame, including identification of the medical procedure from the procedures identified in said medical procedures database, identification of the medical provider from the providers identified in said provider database, and date of the procedure identified from the medical payment claims;
   e. creating a provider history file for each medical provider from said anecdotal data on said computer system;
   f. creating a patient history file for each individual patient from said anecdotal data on said computer system;
   g. iteratively executing a software program referencing each patient history file containing a repetitive medical procedure with each medical provider, wherein a repetitive medical procedure is defined as: 1 the same identified procedure performed on the same patient by a second medical provider after the identified procedure was initially performed by the medical provider, 2 the same identified procedure performed on the same patient after a transfer to a second medical provider after the identified procedure was initially performed by the medical provider, or 3 a second identified procedure to treat a complication arising from the identified procedure, said complication being diagnosed after a transfer to said second medical provider;
   h. determining the percentage of repetitive medical procedures associated with each medical provider as a percentage of all anecdotal data of the same procedure associated with the medical provider;
   i. ranking each medical provider by said percentage of repetitive medical procedures; and
   j. providing a human readable output for each medical provider to said payer for said medical procedures.

2. The method as in claim 1 wherein said deriving step includes identifying the cost associated with each repetitive medical procedure.

3. The method as in claim 2 further comprising identifying multiple payments to an identified medical provider for repetitive medical procedures.

4. A method as defined in claim 1 further comprising;
   a. iteratively executing a database management software program correlating the length of stay at a transferring provider facility for each patient having a repetitive medical procedure after a transfer with the patients payer and payer's maximum compensable time and/or rate;
   b. iteratively executing a software routine for determining a profile for each provider showing transfer histories of patients having a repetitive medical procedure after a transfer based on at least one of: time of day, day of week, proximity to holiday, payer compensable time, and payer compensable rate;
   c. periodically providing human readable copies of such provider profiles to payer for review.

5. A method for determining transfer profiles for medical providers comprising,
   a. creating a procedures database of identified medical procedures in an accessible system memory on a programmable computer;
   b. creating a provider database by associating individual medical providers with a unique identifier in said provider database on said programmable computer;
   c. creating a patient database by associating individual patients with a unique identifier in said patient database on said programmable computer;
   d. deriving anecdotal data for storage in said patient database from sequential medical payment claims relating to an individual patient, including identification of the medical procedure, identification of the medical provider, date of admission for the medical procedure, date of transfer to subsequent medical provider, date of discharge from each medical provider; and payer compensable time and rate information;
   e. creating a provider history file for each medical provider from said anecdotal data on said programmable computer;

f. creating a patient history file for each individual patient from said anecdotal data on said programmable computer;
g. iteratively executing a database management software program correlating the length of stay for each patient with the patients payer and payer's maximum compensable time and/or rate;
h. iteratively executing a software routine for determining a profile for each provider showing transfer histories of patients based on at least one of: time of day, day of week, proximity to holiday, payer compensable time, and payer compensable rate;
i. periodically providing human readable copies of such provider profiles to payer for review.

6. The method as in claim 5 further comprises identifying the cost associated with each medical procedure repeated at a transferee provider.

7. A method as defined in claim 5 further comprising determining at least one of the following as a part of each provider profile relative to patients subjected to a repeated medical procedure by a subsequent provider: length of stay prior to first discharge; length of stay in subsequent provider facility; discharges by day of the week; discharges immediately prior to holidays; mortality rate by provider; demographics by providers identified as a transferor physician; and demographics by providers identified as transferor facilities.

* * * * *